(12) United States Patent
Petrov

(10) Patent No.: US 7,557,225 B2
(45) Date of Patent: Jul. 7, 2009

(54) PROCESS FOR PREPARING HEXAFLUOROISOBUTENE EPOXIDE

(75) Inventor: Viacheslav A. Petrov, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/946,041

(22) Filed: Nov. 27, 2007

(65) Prior Publication Data

US 2008/0177097 A1 Jul. 24, 2008

Related U.S. Application Data

(60) Provisional application No. 60/873,116, filed on Dec. 6, 2006.

(51) Int. Cl.
*C07D 301/08* (2006.01)
(52) U.S. Cl. .................................. 549/523
(58) Field of Classification Search ............ 549/523
See application file for complete search history.

(56) References Cited

U.S. PATENT DOCUMENTS 2,530,309 A * 11/1950 Cook .................. 73/152.56
6,303,800 B1 * 10/2001 Dingerdissen et al. ...... 549/523
6,653,419 B1 11/2003 Petrov et al.

FOREIGN PATENT DOCUMENTS

EP 0209911 4/2008

OTHER PUBLICATIONS

Tarant et al, Fluorine Chemistry Reviews, vol. 5, pp. 77-113, (1971).*
Enantiocontrolled Synthesis of Fluoro-Organic Compounds- Edited by V. A. Soloshonok, Chapter 5, John Wiley & Sons, Ltd., p. 161-164, (1999).*

* cited by examiner

*Primary Examiner*—Bernard Dentz
*Assistant Examiner*—David E Gallis
(74) *Attorney, Agent, or Firm*—Gail D. Tanzer

(57) ABSTRACT

Processes for preparing hexafluoroisobutene epoxide (HFIBO) from $CH_2=C(CF_3)_2$ (HFIB) are provided. The processes can be carried out in substantial absence of oxidation catalysts.

4 Claims, No Drawings

PROCESS FOR PREPARING HEXAFLUOROISOBUTENE EPOXIDE

FIELD OF THE INVENTION

The present invention is directed to a process for preparing 2,2-bis(trifluoromethyl)oxirane (hexafluoroisobutene epoxide, HFIBO).

BACKGROUND

Hexafluoroisobutene epoxide (HFIBO) is a useful intermediate in the synthesis of chemical compounds containing gem-trifluoromethyl groups.

It is currently known to prepare HFIBO by liquid phase oxidation of the corresponding olefin, $CH_2=C(CF_3)_2$, using sodium hypochlorite under phase-transfer catalysis conditions (U.S. Pat. No. 6,653,419).

EP 0 209 911 discloses a process for the oxidation of fluorinated olefins by reacting the olefin with oxygen in the presence of a catalyst.

There is currently a need for a gas-phase process to prepare HFIBO, especially one that does not generate a chlorine waste stream or require the use of a catalyst.

SUMMARY OF THE INVENTION

One aspect of this invention is a process comprising contacting hexafluoroisobutene (HFIB) with oxygen in the substantial absence of oxidation catalysts at a temperature of 200-400° C. and at a pressure of 0.01-100 megapascals.

DETAILED DESCRIPTION

This invention is a gas-phase process for the preparation of HFIBO

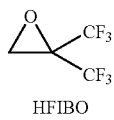
HFIBO from the readily-available olefin, $CH_2=C(CF_3)_2$, and oxygen. The process is typically conducted at temperatures of 200-400° C. and pressures of 0.01-100 megapascals, in the substantial absence of oxidation catalysts.

The process of this invention can be carried out in batch, semi-continuous or continuous mode. The products and unreacted olefin can be isolated by cooling.

In one embodiment, the reaction is carried out in a batch, semi-batch or continuous mode at 210-290° C. and at a pressure of 0.1-100 megapascals for a sufficient time to form a reaction mixture comprising 2,2-bis(trifluoromethyl)oxirane. In another embodiment, the reaction is at 230-270° C. In another embodiment, the reaction is conducted at pressures of 1-50 megapascals. In yet another embodiment, the reaction is conducted at pressures of 1-10 megapascals.

In another embodiment, the reaction can be carried in a continuous mode, in which HFIB and oxygen are contacted in a flow system at atmospheric or sub-atmospheric conditions at 200-400° C. for 1 second to 1 hour.

As illustrated in the Example below, the process of this invention produces the desired epoxide in good yield and selectivity, even in the absence of an oxidation catalyst.

Typical molar ratios of oxygen to olefin range from 1:1 to 10:1. Pure oxygen can be used, or the oxygen can be mixed with other inert gases such as $N_2$ and/or $CO_2$. If a mixture of gases is used, oxygen typically comprises at least 15 mole % of the mixture.

When the process of this invention is conducted in batch mode, the crude products are typically isolated as a liquid phase when the reactor is cooled. In other embodiments, the crude products can be collected by cooling the reaction mixture.

Reaction times vary with reaction temperature and the desired conversion level. Typical reaction times for batch and semi-batch processes range from a few minutes to a few days. As noted, above, reaction times for continuous process can be 5 minutes or less, especially when the reaction is carried out at temperatures above 300° C. Conversion rates of 40-50% are easily achieved, even at relatively high selectivity (30-50% or more) to the desired epoxide.

The crude product typically contains the desired epoxide (HFIBO), as well as unreacted HFIB and hexafluoroacetone (HFA). The HFA can be removed by washing the crude product with water. The desired HFIBO can be isolated by distillation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

HFIB is commercially available from E. I. du Pont de Nemours, Inc. (Wilmington, Del.).

Example 1

A Hastelloy shaker tube (400 mL) was charged with 50 g of $CH_2=C(CF_3)_2$ (HFIB), pressurized with 200 psi of oxygen and was kept at 230° C. for 12 h. The reaction mixture was transferred from the reactor into a cold, evacuated stainless steel cylinder and analyzed by NMR. The crude product contained 2,2-bis(trifluoromethyl)oxirane (HFIBO) (30%), hydrate of hexafluoroacetone (21%), and $CH_2=C(CF_3)_2$ (49%). This corresponds to a conversion of $CH_2=C(CF_3)_2$ of 51%, and a selectivity to epoxide formation of 60%.

Example 2

Example 1 was repeated and the reaction mixtures from 2 consecutive runs were combined and washed with ice water. The water-washed reaction mixture (60 g) was analyzed as liquid by 1H and 19F NMR. The crude product contained 2,2-bis(trifluoromethyl)oxirane (HFIBO) (43%) and $CH_2=C(CF_3)_2$ (57%). Signals attributable to hydrates of hexafluoroacetone were absent in the 19F NMR spectrum. The total calculated yield of epoxides for the 2 combined runs was 25% at 50% conversion of olefin.

What is claimed is:

1. A process comprising contacting $CH_2$=$C(CF_3)2$ with oxygen at a temperature of 200-400° C. and at a pressure of 0.01-100 megapascals for a sufficient time to form a reaction mixture comprising 2,2-bis(trifluoromethyl)oxirane, wherein the contacting is carried out in the substantial absence of an oxidation catalyst.

2. The process of claim 1, wherein the temperature is 230-270° C.

3. The process of claim 1, further comprising washing the reaction mixture with water.

4. The process of claim 1, further comprising purifying the 2,2-bis(trifluoromethyl)oxirane by distillation.

\* \* \* \* \*